United States Patent
Baek

(10) Patent No.: US 9,415,124 B2
(45) Date of Patent: Aug. 16, 2016

(54) BILL STERILIZER EQUIPPED WITH COUNTING MACHINE

(71) Applicant: SMI CO., LTD., Gangwon-do (KR)

(72) Inventor: Myung Soo Baek, Gangwon-do (KR)

(73) Assignee: SMI CO., LTD., Chuncheon-si, Gangwon-do (KR)

( * ) Notice: Subject to any disclaimer, the term of this patent is extended or adjusted under 35 U.S.C. 154(b) by 0 days.

(21) Appl. No.: 14/730,578

(22) Filed: Jun. 4, 2015

(65) Prior Publication Data

US 2015/0359914 A1    Dec. 17, 2015

(30) Foreign Application Priority Data

Jun. 16, 2014   (KR) .......................... 10-2014-0072845

(51) Int. Cl.
*A61L 2/08*      (2006.01)
*G07D 11/00*   (2006.01)
*G07D 13/00*   (2006.01)

(52) U.S. Cl.
CPC ............ *A61L 2/087* (2013.01); *G07D 11/0084* (2013.01); *G07D 13/00* (2013.01); *A61L 2202/11* (2013.01); *A61L 2202/20* (2013.01)

(58) Field of Classification Search
CPC . A61L 2/087; A61L 2202/11; A61L 2202/20; A61L 9/22; G07D 11/0084; G07D 13/00
See application file for complete search history.

(56) References Cited

U.S. PATENT DOCUMENTS

| | | | | |
|---|---|---|---|---|
| 5,504,313 A | * | 4/1996 | Kako ......................... | A61L 2/04 235/379 |
| 5,578,281 A | * | 11/1996 | Kadowaki ................. | A61L 2/04 134/122 R |
| 7,256,979 B2 | * | 8/2007 | Sekoguchi ................. | A61L 9/22 361/231 |
| 2004/0145853 A1 | * | 7/2004 | Sekoguchi ................. | A61L 9/22 361/225 |
| 2005/0053183 A1 | * | 3/2005 | Abe ........................ | B65H 5/062 377/94 |
| 2005/0231884 A1 | * | 10/2005 | Miyaishi ................... | A61L 9/22 361/231 |
| 2007/0045081 A1 | * | 3/2007 | Sugawara ................. | A45C 1/10 194/349 |
| 2007/0080081 A1 | * | 4/2007 | Chang ..................... | A46B 17/06 206/362 |
| 2009/0257912 A1 | * | 10/2009 | Lane ......................... | A61L 2/24 422/24 |
| 2012/0328474 A1 | * | 12/2012 | Campagna ................. | A61L 2/10 422/23 |
| 2013/0001435 A1 | * | 1/2013 | Engelhardt ................ | A61L 2/20 250/455.11 |

FOREIGN PATENT DOCUMENTS

| | | |
|---|---|---|
| KR | 20-0330878 Y1 | 2/2004 |
| KR | 10-0423025 B1 | 3/2004 |
| KR | 20-0464741 Y1 | 1/2013 |

* cited by examiner

*Primary Examiner* — Wyatt Stoffa
(74) *Attorney, Agent, or Firm* — Rabin & Berdo, P.C.

(57) ABSTRACT

A bill sterilizer includes a counting machine having a bill input part, a bill sensing part and a bill discharge part; a body having an opening and a receiving space; a tray provided on the floor of the receiving space; an ion generator located on the wall surface of the receiving space; a door to block the opening of the receiving space; and a door lock located on the front face below the opening of the body to fix the door. The bill sterilizer equipped with the counting machine supplies cluster negative ions to the sterilizer body so that the cluster negative ions are evenly transferred to the surfaces of the bills after the whole counting machine for counting the number of the bills is located inside the bill sterilizer.

3 Claims, 6 Drawing Sheets

BILL STERILIZER EQUIPPED WITH COUNTING MACHINE

BACKGROUND OF THE INVENTION

1. Field of the Invention

The present invention relates to a bill sterilizer, and more particularly, to a bill sterilizer equipped with a counting machine which sterilizes bills through cluster negative ions after the whole counting machine for counting the number of the bills is located inside the bill sterilizer, thereby removing pollution sources of the bills.

2. Background Art

Money is the most fundamental value means which is the basis of the economic structure and has widely run current through bills and coins since ancient times.

Bills are polluted from various pollutants, such as bacteria and dust, more easily than coins while passing lots of distribution channels, and hence, are responsible for spreading bacteria of users who use the bills.

Moreover, bills run current from hand to hand rather than are stored in one place for a long time and are polluted by various bacteria or pathogenic microorganisms in the process and thus serve as the medium that causes or transmits various skin diseases, respiratory diseases and allergic diseases. Therefore, the elderly and young children with weak immune systems may get diseases and persons who handle bills in banks or other financial institutions may be damaged.

In the meantime, bank clerks use bill counting machines because must rapidly calculate and treat the number of lots of bills in banks. Such bill counting machines for calculating the number of bills have a disadvantage in that they cannot sterilize pollutants, such as various bacteria and dust, stained on the bills.

The bill counting machines are divided into various kinds according to methods for counting bills, and most of the bill counting machines calculate the number of moving bills by a sensor while moving bills put on a bill receiver one by one.

The calculated bills are handed to the market again, and are exposed to and polluted by various pollution sources while passing through various hands in various environment so that various bacteria always grow on the surfaces of the bills. The polluted bills become a cause to spread bacteria to many people while passing through various hands.

In order to solve the problem, technology for sterilizing bills has been disclosed.

As one example, Korean Patent No. 10-0423025 published on Mar. 18, 2004 discloses a "bill sterilizing apparatus".

The bill sterilizing apparatus includes: a tray type bill holding unit, on which bills are put, to count and sterilize the bills; a single-sheet feeding unit for conveying the bills put on the bill holder one by one; a bill conveying unit which has a plurality of roller for conveying the bills inserted from the single-sheet feeder and a motor for generating a driving force; a sterilizing unit which has a sprayer for receiving disinfectant from a disinfectant reservoir and spraying the disinfectant onto the bills in order to sterilize the bills conveyed by the bill conveying unit; a drying unit for drying the bills sterilized by the sterilizer; a scent supplier for spraying scent onto the bills passing the drier; a bill holding unit for holding the bills passing the scent supplier; a bill counting unit for detecting the bills and counting the number of the bills while the bills are conveyed by the bill conveying unit; and a controller which has a control circuit for controlling the units and displaying the counted number.

As another example, there is Korean Utility Model Registration No. 20-0330878 published on Feb. 14, 2004 entitled a "sterilizing apparatus for counted bills".

Korean Utility Model Registration No. 20-0330878 relates to a sterilizing apparatus for counted bills which can count, sterilize and disinfect bills at the same time.

That is, the sterilizing apparatus for counted bills includes: a bill counter; an outer case on which the bill counter is mounted; a chemical container which is located inside the outer case and is filled with a disinfectant solution and an air refresher; an electronic valve for controlling outflow of the chemicals; a nozzle for spraying the chemicals; and a connection tube extending from the chemical container to the nozzle. The nozzle is located at an end portion of the connection tube and is connected to a flexible connection tube which is adjustable in position to sterilize the counted bills before they are stacked up.

Furthermore, Korean Utility Model Registration No. 20-0464741 discloses a "sterilized bill counting machine" published on Jan. 21, 2013.

The sterilized bill counting machine includes a conveyer for conveying bills put thereinto and UV sterilizing lamps mounted to sterilize the bills. The UV lamps are located at an upper portion and a lower portion of the conveyer and are spaced apart from each other at an interval of 1 mm to 2 mm. The UV lamp has an arc-shaped reflector mounted on the outer circumference thereof to intensively irradiate ultraviolet rays onto the bills. In this instance, the two 11-watt UV lamps are respectively mounted at the upper portion and the lower portion of the conveyer, and the reflector of the UV lamp forms an arc-shaped part which is bent upwardly at the side where the bills are put in so as to prevent the bills from being caught to the reflector when being put in.

PATENT LITERATURE

[Patent Literature 1] Korean Patent No. 10-0423025 published on Mar. 18, 2004

[Patent Literature 1] Korean Utility Model Registration No. 20-0330878 published on Feb. 14, 2004

[Patent Literature 1] Korean Utility Model Registration No. 20-0464741 published on Jan. 21, 2013

SUMMARY OF THE INVENTION

Accordingly, the present invention has been made to solve the above-mentioned problems occurring in the prior arts, and it is an object of the present invention to provide a bill sterilizer equipped with a counting machine which supplies cluster negative ions to the sterilizer body so that the cluster negative ions are evenly transferred to the surfaces of the bills after the whole counting machine for counting the number of the bills is located inside the bill sterilizer, thereby removing pollution sources of the bills.

To accomplish the above object, according to the present invention, there is provided a bill sterilizer equipped with a counting machine including: a counting machine which has a bill input part, a bill sensing part and a bill discharge part; a body which has an opening formed at one side and a receiving space formed to receive the counting machine therein; and an ion generator which is located on the wall surface of the receiving space and sprays cluster negative ions with a sterilizing function toward bills to sterilize bills.

The bill sterilizer further includes a tray which is provided on the floor of the receiving space, moves forward and backward through rails to go in and out through the opening and on which the counting machine is put.

Additionally, the bill sterilizer further includes: a door of which the top is fixed and wound onto a winding reel with a corrective elastic force rotatably combined above the opening of the receiving space and which blocks the opening of the receiving space when it is released; and a door lock which is located on the front face below the opening of the body to fix the door.

Moreover, the ion generator includes: an ion generating part which is disposed in the body to generate cluster negative ions; an ion spraying part for spraying the cluster negative ions generated in the ion generating part to the receiving space; a joint part which is disposed on the body and has a plurality of joint bars connected to each other so as to do a joint movement and to be folded and unfolded; a diffusion sprayer which is disposed at the front end of the joint part, has the form that becomes gradually wider from an inlet to an outlet and is located at the bill discharge part of the counting machine when the joint part is spread; and a tube of which one end is connected to the ion generating part and the other end is connected to the diffusion sprayer to sterilize the bill by transmitting the cluster negative ions generated in the ion generating part to the diffusion sprayer.

Furthermore, a camera is disposed on the inner wall of the receiving space and a digital display part for displaying an image of the camera in real time is disposed on the outer face of the body.

Additionally, the door is made of a transparent material and is coated with photocatalyst.

The bill sterilizer equipped with the counting machine according to the present invention supplies cluster negative ions to the sterilizer body so that the cluster negative ions are evenly transferred to the surfaces of the bills after the whole counting machine for counting the number of the bills is located inside the bill sterilizer, thereby removing pollution sources of the bills.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Figure 1:
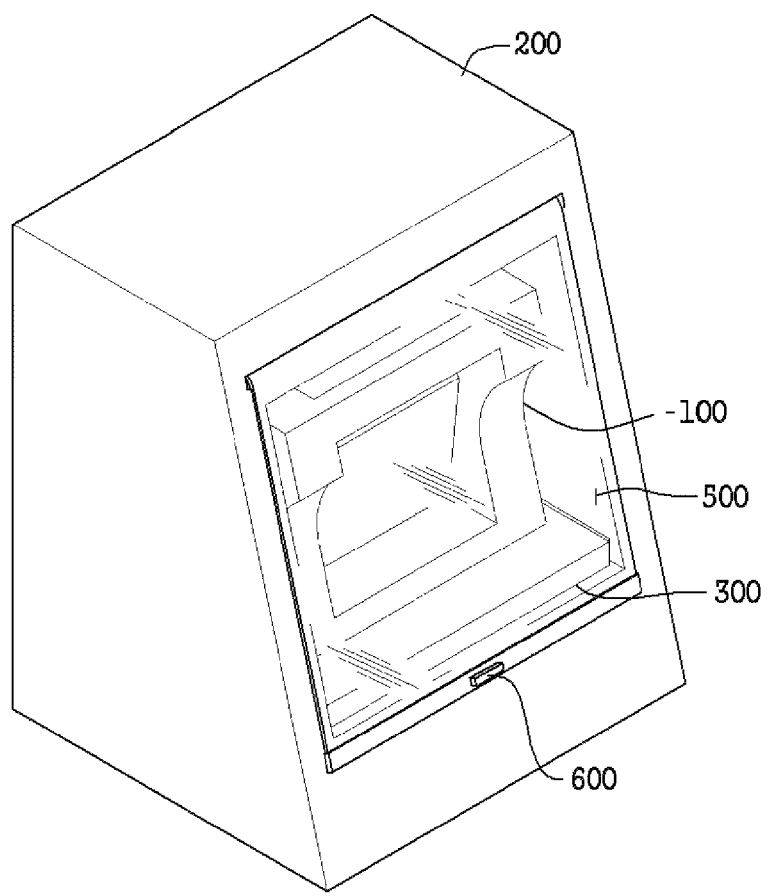
FIG. 1 is a perspective view of a bill sterilizer equipped with a counting machine according to a preferred embodiment of the present invention.
Figure 2:
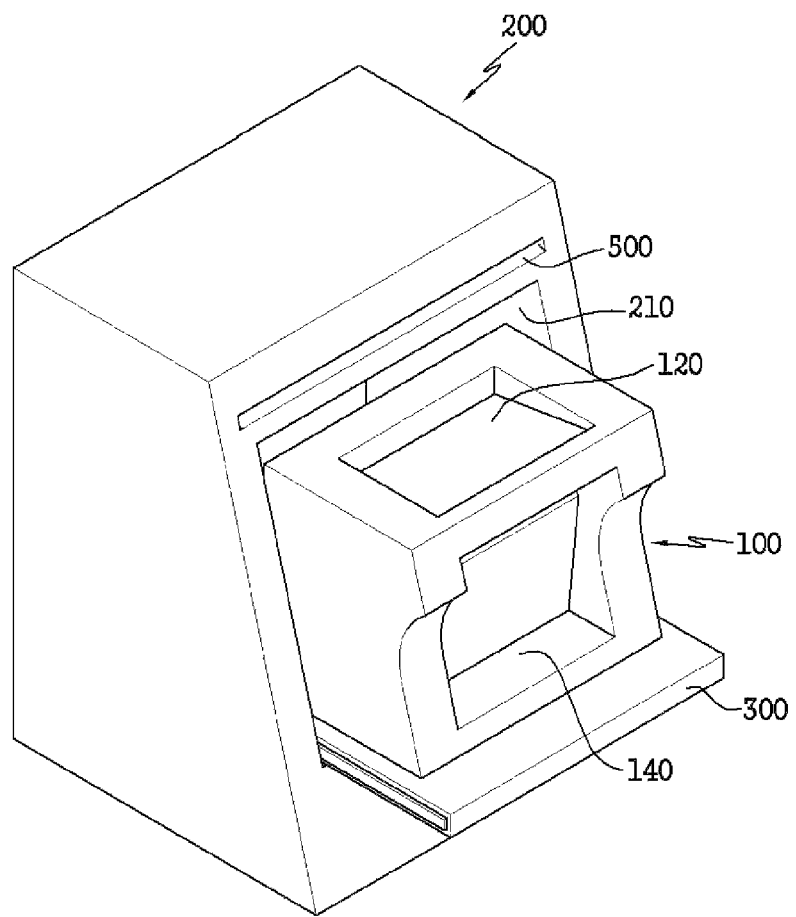
FIG. 2 is a view showing a used state of the bill sterilizer in the process that the counting machine is seated on the bill sterilizer of FIG. 1.
Figure 3:
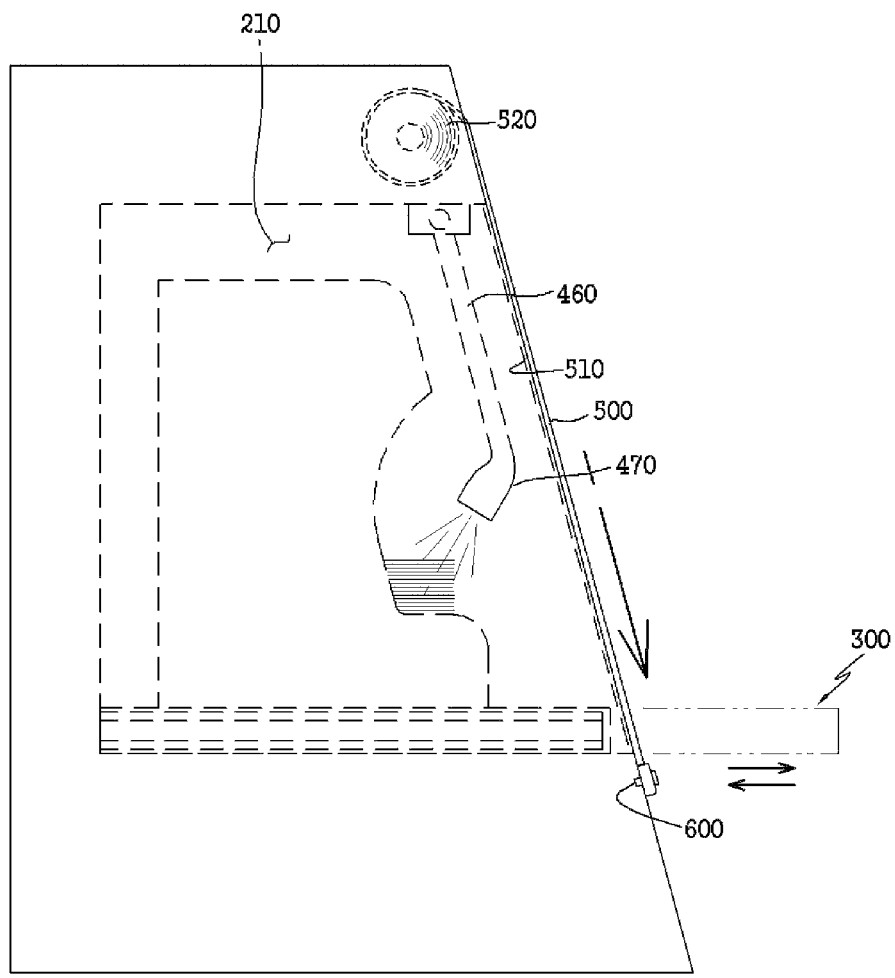
FIG. 3 is a side view of FIG. 1.
Figure 4:
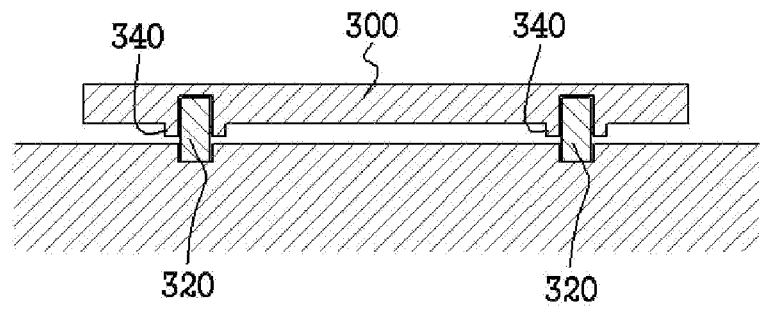
FIG. 4 is a front sectional view of essential parts of FIG. 3.
Figure 5:
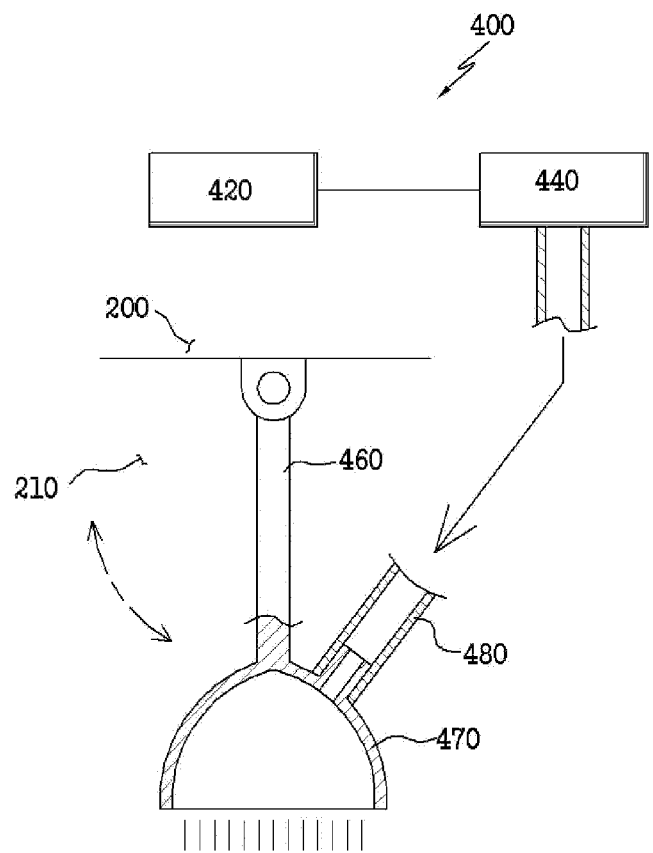
FIG. 5 is a view showing an operational state of an ion generator of FIG. 1.

Hereinafter, reference will be now made in detail to the preferred embodiment of the present invention with reference to the attached drawings. In the description of the present invention, when it is judged that detailed descriptions of known functions or structures related with the present invention may make the essential points vague, the detailed descriptions of the known functions or structures will be omitted. In addition, in the drawings, the same components have the same reference numerals even though they are illustrated in different figures.

As shown in FIGS. 1 to 5, a bill sterilizer equipped with a counting machine according to the preferred embodiment of the present invention includes: a counting machine 100 for counting the number of bills; a body 200 for receiving the counting machine 100; a tray 300 for guiding the counting machine 100 to the body 200 so that the counting machine 100 is accommodated in the body 200; an ion generator 400 for supplying cluster negative ions into the body 200; a door 500 for selectively blocking the inside of the body 200; and a door lock 600 for locking the door 500 to the body 200.

The counting machine 100 is well-known means which has been generally used, and includes: a bill input part 120 formed at one side for inputting bills which will be counted in number; and a bill discharge part 140 formed at the other side for discharging the bills. Moreover, the counting machine 100 further includes a bill sensing unit which is also well-known means to sense the number of the conveyed bills.

The body 200 includes: an opening which is formed at one side and has the size that the counting machine 100 can go in and out; and a receiving space 210 in which the counting machine 100 is accommodated and seated.

The tray 300 is disposed on the floor of the receiving space 210 to support the bottom surface of the counting machine 100 and moves forward and backward through rails 320 formed on the floor so as to go in and out through the opening of the body 200. The counting machine 100 is put on the upper surface of the tray 300.

That is, a pair of groove type or protrusion type rails 320 are formed on the floor of the receiving space 210, and the tray 300 has guiders 340 which are disposed on the bottom surface of the tray 300 to slide along the rails 320 so that the guiders 340 can slide along the rails 320.

Therefore, when a user pulls the tray 300 located on the floor of the receiving space 210 of the body 200 and puts the counting machine 100 on the tray 300, the counting machine 100 is easily accommodated in the body 200.

The ion generator 400 is located on the wall surface of the receiving space 210, and sprays cluster negative ions with sterilizing function toward the bills at the time of an electrical action.

Now, the structure of the ion generator 400 will be described. The ion generator 400 includes: an ion generating part 420 which is disposed in the body 200 to generate cluster negative ions; and an ion spraying part 440 for spraying the cluster negative ions generated in the ion generating part 420 to the receiving space 210.

The ion spraying part 440 includes: a joint part 460 whose one end is hinged to the body 200 to be rotated; a diffusion sprayer 470 which is disposed at the front end of the joint part 460, has the form that becomes gradually wider from an inlet to an outlet and is located at the bill discharge part 140 of the counting machine 100 when the joint part 460 is rotated or spread; and a tube of which one end is connected to the ion generating part 420 and the other end is connected to the diffusion sprayer 470 to sterilize the bill by transmitting the cluster negative ions generated in the ion generating part 420 to the diffusion sprayer 470.

The diffusion sprayer 470 is connected to the end portion of the joint part 460 by a ball joint to be able to rotate, and comes into contact with the wall surface of the receiving space 210 of the body 200 when it is stored and is located in such a way that the spray direction of the diffusion sprayer 470 faces the bills when it is used.

The joint part 460 has one or more joint bars, and locates the diffusion sprayer 470 of the front end thereof to be close to the bills by a joint movement when it is spread in a state where it gets in close contact with the inner wall surface of the body 200.

The door 500 may be made of cloth or synthetic resin of a flexible material, and the top of the door 500 is fixed and wound onto a winding reel 520 with a corrective elastic force rotatably combined above the opening of the receiving space 210, and the door 500 blocks the opening of the receiving space 210 when it is released.

The winding reel 520 is a known technology, and includes a plate spring wound on a fixed shaft and a sheet which forms the door and is connected to an end portion of the plate spring so as to be automatically wound by a winding force of the plate spring.

The door lock 600 is located on the front face below the opening of the body 200 to selectively lock and unlock the door 500.

In other words, the door 500 is drawn out downwardly to close the receiving space 210 when the ion generator 400 is operated. However, when the door lock 600 is released after sterilization of the bills, the door 500 is automatically wound by the winding reel 520 to open the door 500.

Figure 6:
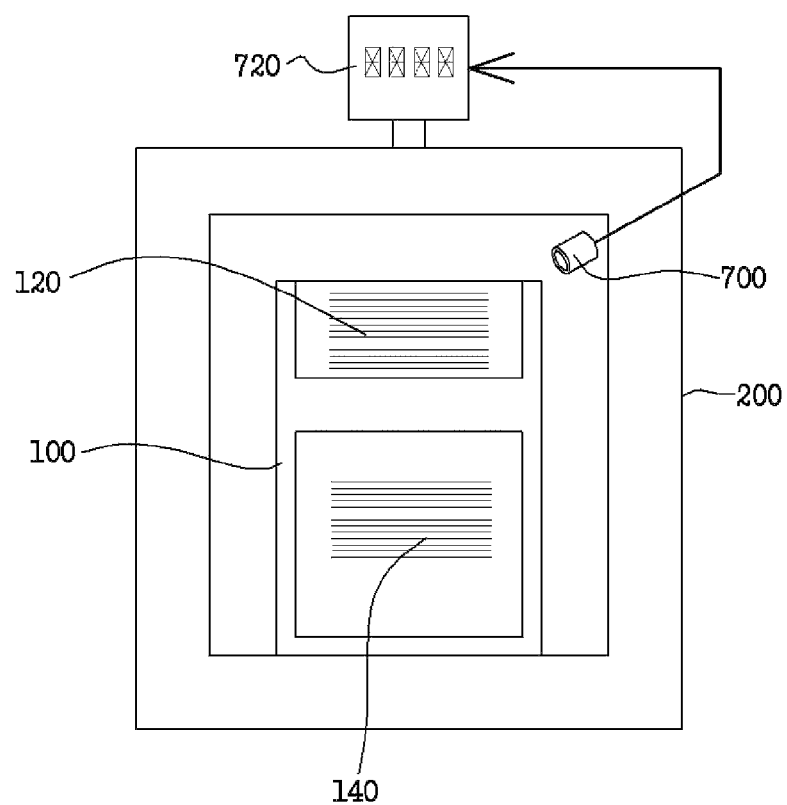
FIG. 6 is a view of a camera for photographing bills in FIG. 1.

FIG. 6 shows another example of the present invention. In FIG. 6, a camera 700 is mounted on the inner wall of the receiving space 210.

Additionally, a digital display part 720 for displaying an image of the camera 700 in real time is disposed on the outer face of the body 200.

Figure 7:
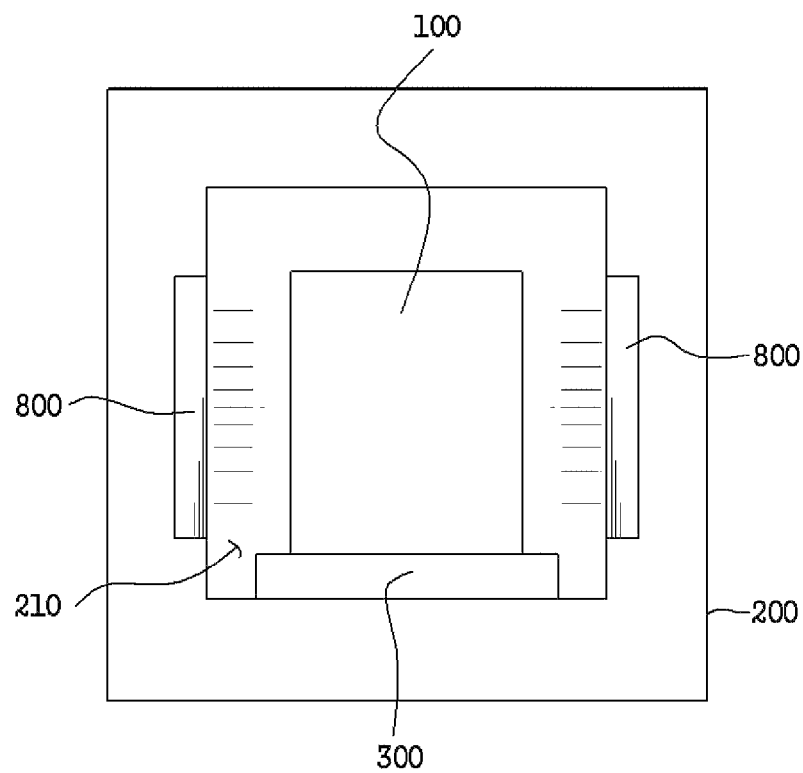
FIG. 7 is a view showing a state where the bill sterilizer of FIG. 1 includes UV lamps.

FIG. 7 shows a further example of the present invention. In FIG. 7, UV lamps 800 are combined to the inside of the body 200.

Here, the door 500 may be made of a transparent material and may be coated with photocatalyst 510.

The UV lamps 800 are fit into sockets mounted at both sides of the inside of a reflection board to irradiate ultraviolet rays. The irradiated ultraviolet rays can sterilize various bacteria without any change in the bills. The sockets are electrically connected to be supplied with electric power.

The photocatalyst 510 is in a solid or liquid state and is coated on the surface of the door 500. Moreover, the photocatalyst 510 produces a catalytic reaction using ultraviolet rays irradiated from the UV lamps as a source of energy so as to sterilize various bacteria stained on the bills. The photocatalyst 510 generates active oxygen when reacting with the irradiated ultraviolet rays, thereby sterilizing various germs, such as colon bacillus, bacteria, molds and virus and decomposing nicotine and smell of cigarette.

The ion generating part 420 of the ion generator 400 generates positive ions and negative ions through high frequencies. The positive ions and the negative ions ionize and generate moisture in the air by high-frequency oscillation and make cluster ions that a plurality of water molecules are attached around hydrogen ions and oxygen ions. The generated ions are gathered around particles formed on the surfaces of the bills to cause a chemical reaction, thereby serving a sterilizing action.

As described above, while the present invention has been particularly shown and described with reference to the preferable embodiment thereof, it will be understood by those of ordinary skill in the art that the present invention is not limited to the above embodiment and various changes may be made therein without departing from the technical idea of the present invention. For example, the forms and structures of the components described in the preferred embodiment of the present invention may be changed or modified.

What is claimed is:

1. A bill sterilizer equipped with a counting machine comprising:
   a counting machine which has a bill input part, a bill sensing part and a bill discharge part;
   a body which has an opening formed at one side and a receiving space formed to receive the counting machine therein; and
   an ion generator which is located on a wall surface of the receiving space and sprays cluster negative ions with a sterilizing function toward bills to sterilize bills, the ion generator including
      an ion generating part which is disposed in the body to generate the cluster negative ions,
      an ion spraying part for spraying the cluster negative ions generated in the ion generating part to the receiving space,
      a joint part which is disposed on the body and has a plurality of joint bars connected to each other so as to do a joint movement and to be folded and unfolded,
      a diffusion sprayer which is disposed at a front end of the joint part, has a form that becomes gradually wider from an inlet to an outlet, and is located at the bill discharge part of the counting machine when the joint part is spread, and
      a tube of which one end is connected to the ion generating part and the other end is connected to the diffusion sprayer to sterilize the bill by transmitting the cluster negative ions generated in the ion generating part to the diffusion sprayer.

2. The bill sterilizer according to claim 1, wherein a camera is disposed on an inner wall of the receiving space and a digital display part for displaying an image of the camera in real time is disposed on an outer face of the body.

3. The bill sterilizer according to claim 1, further comprising:
   a tray which is provided on a floor of the receiving space, moves forward and backward through rails to go in and out through the opening and on which the counting machine is put;
   a door of which a top is rotatably combined onto a winding reel with a corrective elastic force above the opening of the receiving space and which blocks the opening of the receiving space when it is released; and
   a door lock which is located on a front face below the opening of the body to fix the door.

* * * * *